US006569870B1

(12) United States Patent
Lee et al.

(10) Patent No.: US 6,569,870 B1
(45) Date of Patent: May 27, 2003

(54) FLUORINATED QUINOLONES AS ANTIMITOTIC AND ANTITUMOR AGENTS

(75) Inventors: Kuo-Hsiung Lee; Yi Xia; Zheng-Yu Yang, all of Chapel Hill, NC (US); Sheno-Chu Kuo, Taichang (TW)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 09/669,155

(22) Filed: Sep. 25, 2000

(51) Int. Cl.[7] ..................... A61K 31/47; C07D 215/16; C07D 215/20
(52) U.S. Cl. ................ 514/312; 514/314; 546/153; 546/155
(58) Field of Search ................ 514/312, 314; 546/153, 155

(56) References Cited

FOREIGN PATENT DOCUMENTS

WO        WO 96/10563        4/1996

OTHER PUBLICATIONS

Zhang, CA 132:189292, 2000.*
Brown, CA 128:61434, 1997.*
Hsieh, CA 129:260328, 1998.*
Staskun, CA 129:260329, 1998.*
Velezheva, CA 117:233816, 1992.*
Li, CA 121:255614, 1994.*
Zhang, Shun–Xiang, et al., *Antitumor Agents. 199. Three–Dimensional Quantitative Structure–Activity Relationship Study of the Colchicine Binding Site Ligands Using Comparative Molecular Field Analysis*, J. Med. Chem., vol. 43, pp. 167–176 (2000).
Zia, Yi, et al., *Antitumor Agents. 211. Fluorinated 2–Phenyl–4–quinolone Derivaties as Antimitotic Antitumor Agents*, J. Med. Chem., vol. 44, pp. 3932–3936 (2001).
Kaye, Perry T., et al., Abstract, *Mass spectrometric analysis of 2–phenyl–1,2,3,4–tetrahydro–1,4–benzodiazepin–5–ones and their tetrazolo[1,5–d]derivatives*, J. Chem. Res., Synop, vol. 62, No. 3, pp. 367–82 (1994).

* cited by examiner

Primary Examiner—D. Margaret Seaman
(74) Attorney, Agent, or Firm—Myers Bigel Sibley & Sajovec

(57) ABSTRACT

The present invention provides fluorinated quinolones which are fluorinated on the phenyl group thereof, along with pharmaceutical formulations containing the same, methods of treating tumors or cancer by the administration of such compounds, and methods of inhibiting cellular mitosis by the administration of such compounds.

31 Claims, 4 Drawing Sheets

FIG. 2 SCHEME 1

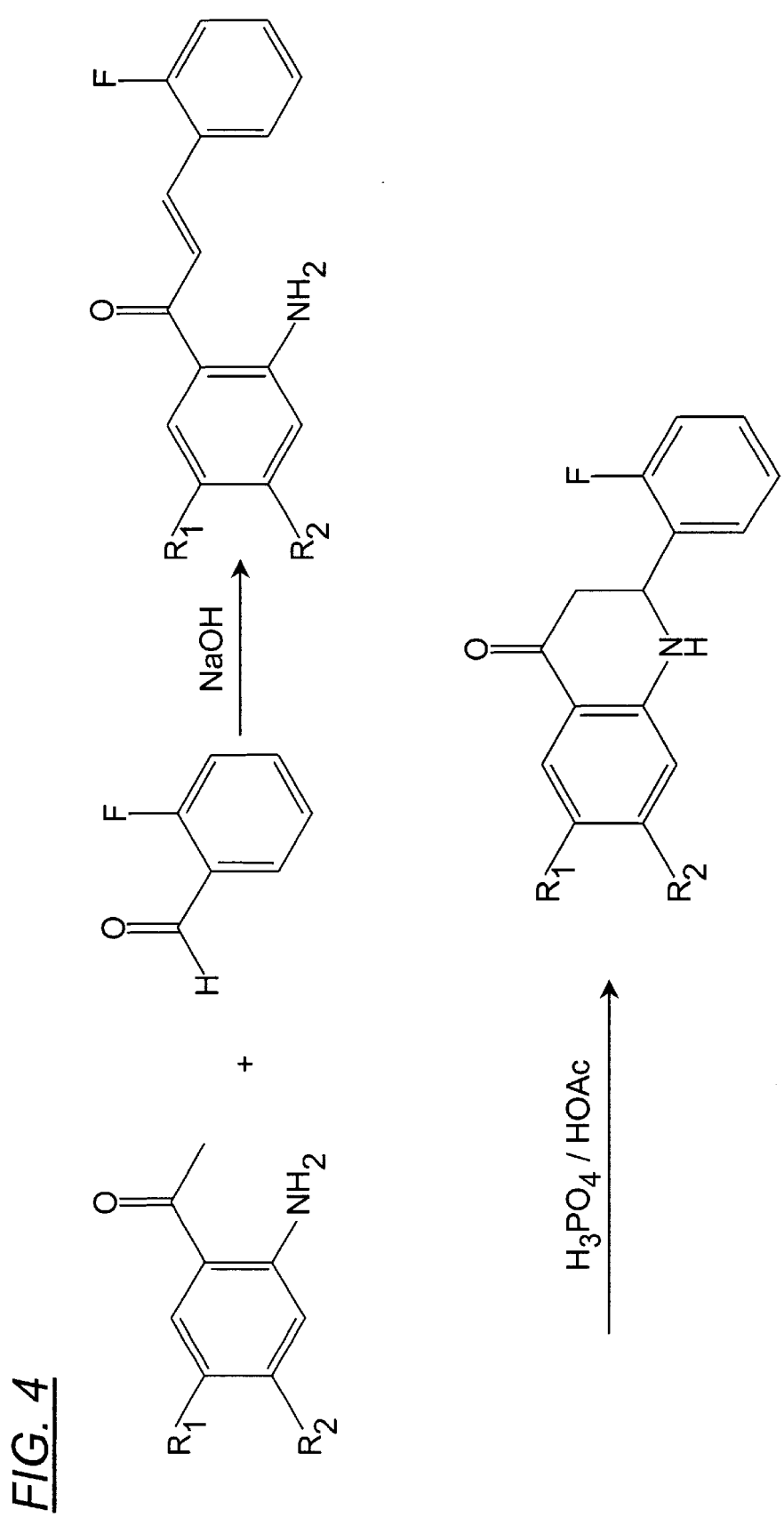
FIG. 4    SCHEME 3

FLUORINATED QUINOLONES AS ANTIMITOTIC AND ANTITUMOR AGENTS

This invention was made with government support under Grant Number CA-17625 from the National Cancer Institute. The government has certain rights to this invention.

FIELD OF THE INVENTION

The present invention concerns quinolone derivatives, pharmaceutical formulations containing the same, and methods of use thereof as antimitotic and antitumor agents, particularly for the treatment of tumors such as breast cancer and ovarian cancer.

BACKGROUND OF THE INVENTION

Microtubules are one of the most important subcellular targets for the development of anticancer chemotherapeutic compounds. Vinca alkaloids and taxoids are well-known examples of antimitotic agents that are widely used clinically to treat different cancers (E. Rowinsky et al., *Pharmacol. & Ther.* 1992, 52, 35–84; J. Verweij et al., *Ann. Oncol.* 1994, 5, 495–505). Colchicine (FIG. 1) is another well-known agent that inhibits microtubule assembly (S. Hastie, *Pharm. & Ther.* 1991, 51, 377–401; S. Hastie, *Pharm. & Ther.* 1991, 51, 377–401). Although colchicine has limited utility for cancer therapy, the drug has been an important tool in studies of microtubule structure and function. The vinca alkaloids, taxoids, and colchicine each interact with tubulin by a unique mechanism, probably involving distinct binding sites on the protein.

The synthesis and biological evaluation of a series of 2-phenyl-4-quinolones as antimitotic and antitumor agents has been reported (S. Kuo et al., *J. Med. Chem.* 1993, 36, 1146–1156; L. Li et al., *J. Med. Chem.* 1994, 37, 1126–1135; L. Li et al., *J. Med. Chem.* 1994, 37, 3400–3407). The compounds were evaluated in the National Cancer Institute's 60 human tumor cell line (HTCL) in vitro screen and in a tubulin polymerization inhibition assay. Most compounds showed cytotoxicity in the HTCL screen, with $GI_{50}$ values in the low micromolar to nanomolar concentration range. In general, a good correlation was found between cytotoxicity and inhibition of tubulin polymerization. SAR studies led to the discovery of 2'-fluoro-6,7-methylenedioxy-2-phenyl-4-quinolone (Compound 1; FIG. 1) (L. Li et al., *J. Med. Chem.* 1994, 37, 1126–1135), which showed cytotoxicity with an average log $GI_{50}$ value of −6.47 (log concentration which reduced cell growth by 50%) in the HTCL screen. Compound 1 was also an inhibitor of tubulin polymerization, with an $IC_{50}$ value of 0.85 μM. Compound 1 also demonstrated good in vivo activity against the OVCAR-3 ovarian cell line, prolonging the life span of mice bearing the tumor by 130%.

Accordingly, an object of the present invention is to develop additional compounds that can be used as antimitotic agents, antitumor agents, or both.

SUMMARY OF THE INVENTION

A first aspect of the present invention is, accordingly, a compound according to Formula I, or a pharmaceutically acceptable salt thereof:

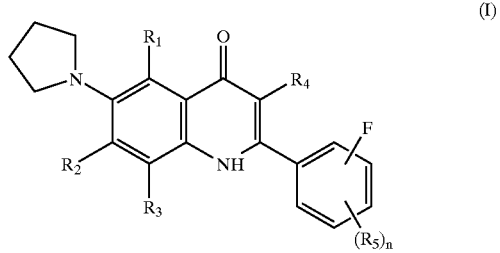

wherein:
  $R_1$ is selected from the group consisting of H, hydroxy, lower alkyl, lower alkoxy, hydroxy, halo, and amino (preferably H or lower alkyl; most preferably H);
  $R_2$ is is selected from the group consisting of H, hydroxy, lower alkyl, lower alkoxy, hydroxy, halo, and amino (preferably H or lower alkyl; most preferably H);
  $R_3$ is is selected from the group consisting of H, hydroxy, lower alkyl, lower alkoxy, hydroxy, halo, and amino (preferably H or lower alkyl; most preferably H);
  $R_4$ is is selected from the group consisting of H, hydroxy, lower alkyl, lower alkoxy, hydroxy, halo, and amino (preferably H or lower alkyl; most preferably H);
  $R_5$ is is selected from the group consisting of H, hydroxy, lower alkyl, lower alkoxy, hydroxy, halo, and amino (preferably H or lower alkyl; most preferably H); and
  n is 0, 1, 2, 3 or 4 (it being understood that, when n is 0, then all positions are substituted by H).

Preferably F is substituted on the phenyl group at the ortho position, or multi-F substituted at the ortho and other positions, as in a compound of the structure:

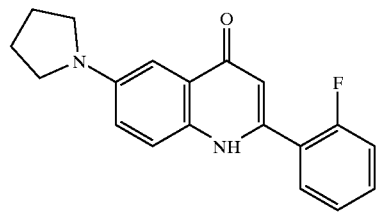

or a pharmaceutically acceptable salt thereof.

A second aspect of the present invention is a pharmaceutical formulation comprising or consisting essentially of a compound according to Formula I, or a pharmaceutically acceptable salt thereof, in a pharmaceutically acceptable carrier (e.g., an aqueous carrier).

A third aspect of the present invention is a method for treating a tumor comprising administering to a subject in need of such treatment a treatment effective amount of a compound of Formula I, or a pharmaceutically acceptable salt thereof.

A fourth aspect of the present invention is a method of inhibiting cellular mitosis, comprising: contacting a cell with a compound of Formula I, or a pharmaceutically acceptable salt thereof, in an amount effective to inhibit cellular mitosis.

A fifth aspect of the present invention is a compound according to Formula II, or a pharmaceutically acceptable salt thereof:

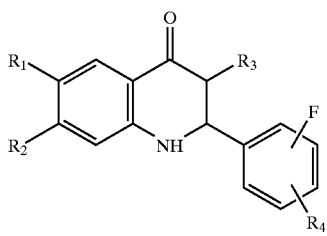

(II)

wherein:
R₁ is selected from the group consisting of H, hydroxy, lower alkyl, lower alkoxy, halo, amino, and heterocyclic rings;

R₂ is selected from the group consisting of H, hydroxy, lower alkyl, lower alkoxy, halo, and amino (preferably H or loweralkyl; most preferably H);

R₃ is selected from the group consisting of H, hydroxy, lower alkyl, lower alkoxy, halo, and amino (preferably H or loweralkyl; most preferably H); and R₄ is selected from the group consisting of H, hydroxy, lower alkyl, lower alkoxy, halo, and amino (preferably H or loweralkyl; most preferably H).

Preferably F is substituted on the phenyl group at the ortho position, or multi-F substituted on the phenyl group at the ortho and other positions, as in a compound of the structure:

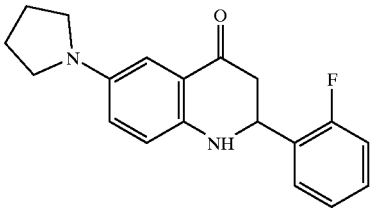

or a pharmaceutically acceptable salt thereof.

A sixth aspect of the present invention is a pharmaceutical formulation comprising or consisting essentially of a compound according to Formula II, or a pharmaceutically acceptable salt thereof, in a pharmaceutically acceptable carrier (e.g., an aqueous carrier).

A seventh aspect of the present invention is a method for treating a tumor comprising administering to a subject in need of such treatment a treatment effective amount of a compound of Formula II, or a pharmaceutically acceptable salt thereof.

An eighth aspect of the present invention is a method of inhibiting cellular mitosis, comprising: contacting a cell with a compound of Formula II, or a pharmaceutically acceptable salt thereof, in an amount effective to inhibit cellular mitosis.

The foregoing and other objects and aspects of the present invention are explained in detail in the drawings herein and the specification set forth below.

BRIEF DESCRIPTION OF THE DRAWINGS

FIG. 4 illustrates a third scheme, Scheme 3, for making compounds of the present invention.

DETAILED DESCRIPTION OF THE PREFERRED EMBODIMENTS

Figure 1:
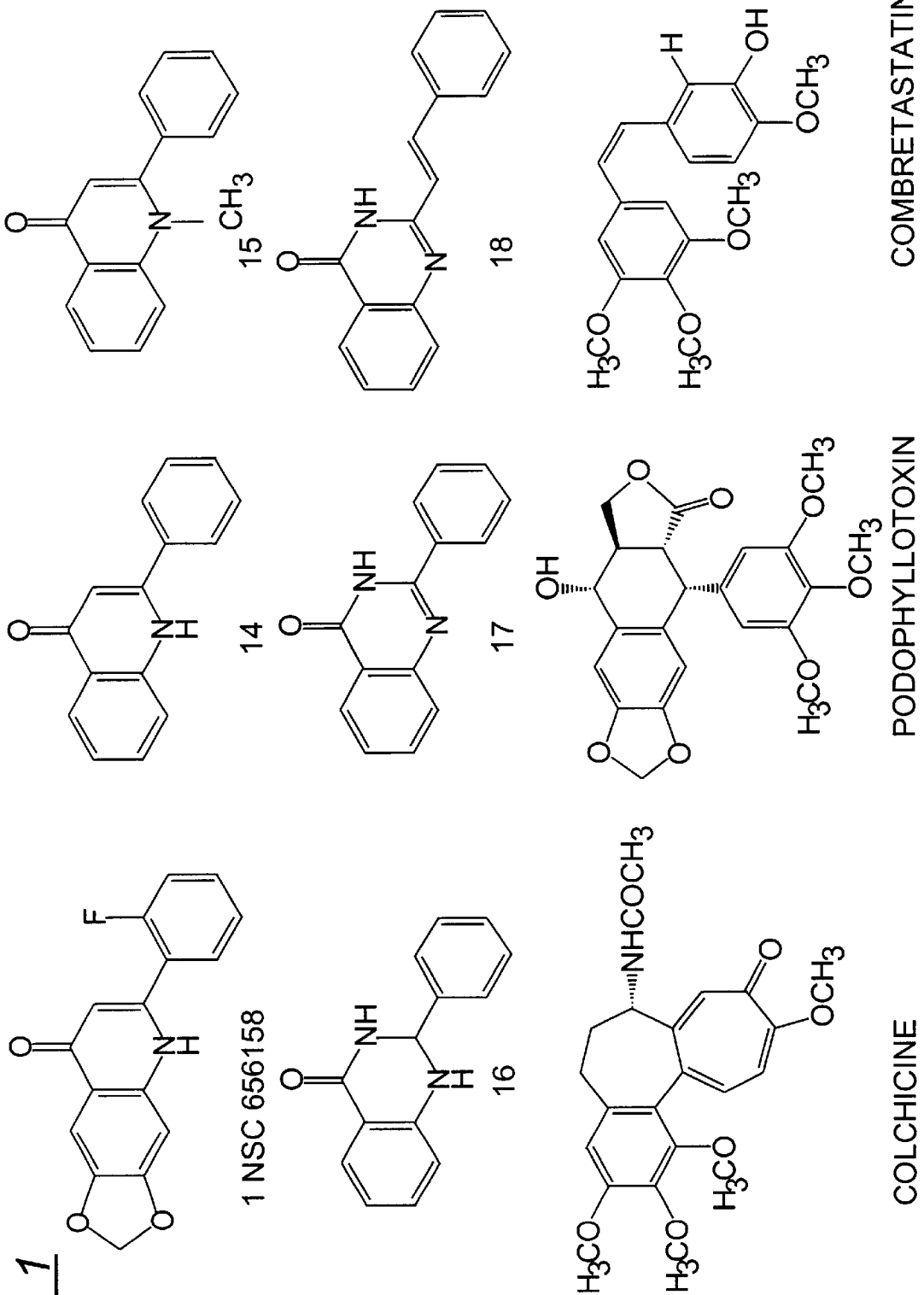
FIG. 1 illustrates certain compounds of the present invention and certain compounds of the prior art.

"Alkyl" as used herein refers to linear or branched, saturated or unsaturated hydrocarbon chains, including for example, methyl, ethyl, propyl, isopropyl, butyl, isobutyl, and tert-butyl groups.

"Alkoxy" as used herein refers to linear or branched, saturated or unsaturated oxo-hydrocarbon chains, including for example methoxy, ethoxy, propoxy, isopropoxy, butoxy, and t-butoxy.

"Amino" as used herein refers to the substituent —NR₁R₂, where R₁ and R₂ are each independently selected from the group consisting of H and C1–C4 alkyl.

"Halo," "halide," or "halogen" as used herein refer to fluorine, chlorine, bromine, and iodine.

"Heterocyclic rings" as used herein refers to any heterocyclic ring, particularly 5 or 6 member heterocyclic rings containing one or two hetero atoms selected from the group consisting of N, S, and O.

"Treat" or "treating" as used herein refers to any type of treatment that imparts a benefit to a patient afflicted with a disease, including improvement in the condition of the patient (e.g., in one or more symptoms), delay in the progression of the disease, etc.

"Pharmaceutically acceptable" as used herein means that the compound or composition is suitable for administration to a subject to achieve the treatments described herein, without unduly deleterious side effects in light of the severity of the disease and necessity of the treatment.

1. Active Compounds.

Synthesis of 2'-fluoro-6,7-methylenedioxy-2-phenyl-4-quinolone (1) was previously reported (L. Li et al., *J. Med. Chem.* 1994, 37, 1126–1135). The synthesis of enol ether derivatives (2–5) is shown in Scheme 1. Treatment of 1 with NaH in DMF followed by alkylation with ethyl chloroacetate or ethyl-4-chlorobutyrate afforded 2 and 4. Hydrolysis of 2 and 4 with 10% NaOH in MeOH gave carboxylic acids 3 and 5, respectively. Treating 1 with Lawesson's reagent in toluene gave thioketone 6. The nitrogen atom in 1 was converted to the carbamate (7) with tert-butoxycarbonyl (Boc) in CH₂Cl₂ at room temperature.

Figure 2:
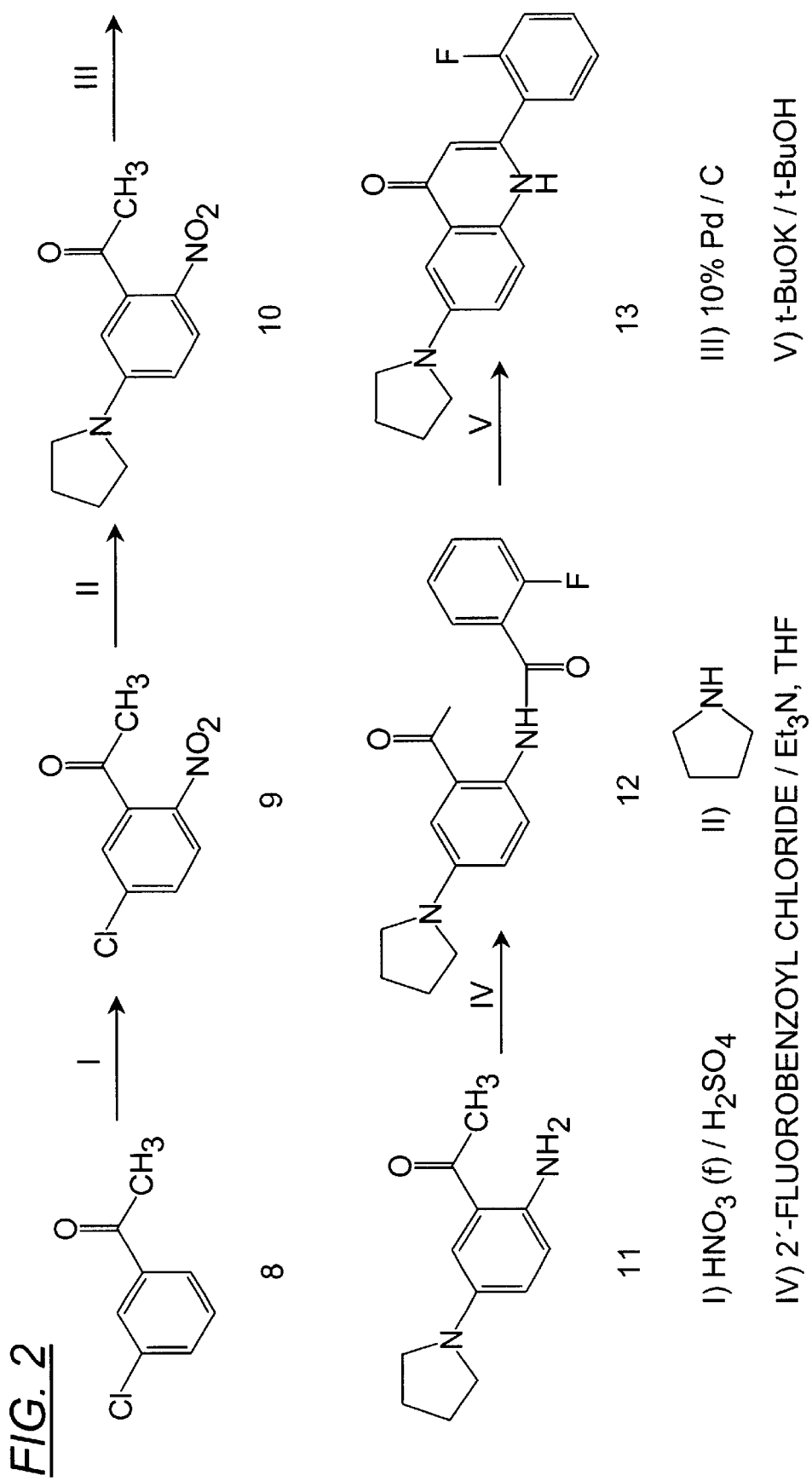
FIG. 2 illustrates a first scheme, Scheme 1, for making compounds of the present invention.
Figure 3:
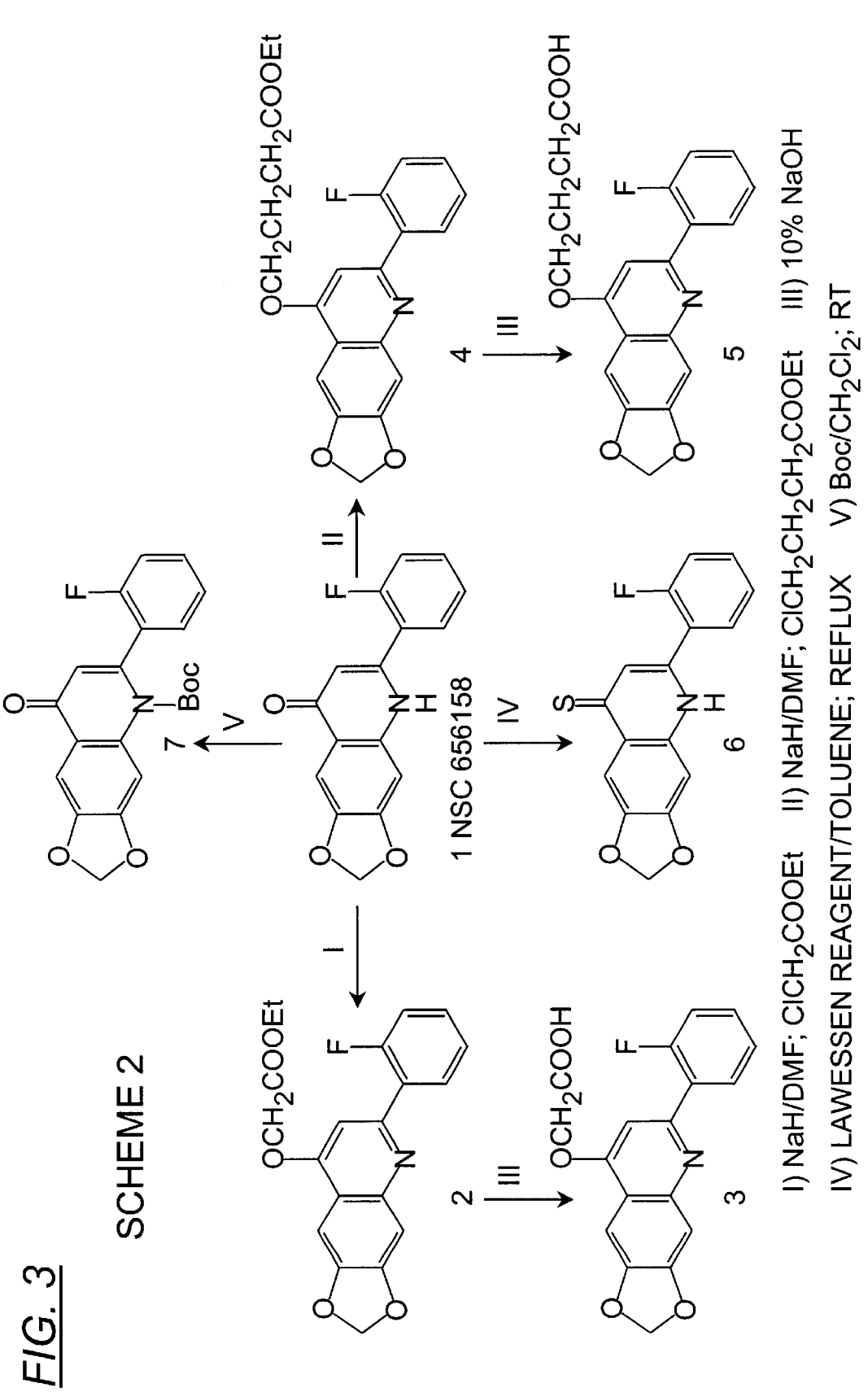
FIG. 3 illustrates a second scheme, Scheme 2, for making compounds of the present invention.

Synthesis of 13 (FIG. 2) was based on a literature method (L. Li et al., *J. Med. Chem.* 1994, 37, 1126–1135). Nitration of 3'-chloroacetophenone (8) gave 2'-nitro-5'-chloroacetophenone. Nucleophilic displacement of the 5'-chloro group by pyrroline followed by hydrogenation gave 11. The biaryl amide (12) was formed from condensation of 11 and 2-fluorobenzoylchloride in THF. Cyclization of 12 in the presence of tert-butoxide (t-BuOK) gave 13.

Preparation of compounds shown in FIG. 4, may be carried out by condensation of the appropriate 2-amino acetophenone and 2-fluoro benzaldehyde, followed by acid-catalyzed cyclization to give the final products.

The active compounds disclosed herein can, as noted above, be prepared in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

2. Pharmaceutical Formulations.

The active compounds described above may be formulated for administration in a pharmaceutical carrier in accordance with known techniques. See, e.g., Remington, *The Science And Practice of Pharmacy* ($9^{th}$ Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy consisting essentially of admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound, which preparations are preferably isotonic with the blood of the intended recipient. These preparations may contain antioxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising a compound of Formula (I), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to compounds of formula (I) or their salts, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

3. Dosage and Routes of Administration.

The active compounds described herein inhibit tubulin polymerization and/or have antimitotic activity. Such compounds are useful for the treatment of conditions including psoriasis, gout, papiloma, warts, and various tumors, particularly solid tumors, including but not limited to lung cancer (e.g., non-small cell lung cancer), colon cancer, central nervous system cancers, melanoma, ovarian cancer, prostate cancer and breast cancer.

Subjects to be treated by the methods of the present invention are typically human subjects although the methods of the present invention may be useful with any suitable subjects known to those skilled in the art, and particularly mammalian subjects including, in addition to humans, horses, cows, dogs, rabbits, fowl, sheep, and the like. As noted above, the present invention provides pharmaceutical formulations comprising the compounds of Formula I, or pharmaceutically acceptable salts thereof, in pharmaceutically acceptable carriers for oral, rectal, topical, buccal, parenteral, intramuscular, intradermal, or intravenous, and transdermal administration.

The therapeutically effective dosage of any specific compound, the use of which is in the scope of present invention, will vary somewhat from compound to compound, patient to patient, and will depend upon the condition of the patient and the route of delivery. As a general proposition, a dosage from about 0.1 to about 50 mg/kg will have therapeutic efficacy, with still higher dosages potentially being employed for oral and/or aerosol administration. Toxicity concerns at the higher level may restrict intravenous dosages to a lower level such as up to about 10 mg/kg, all weights being calculated based upon the weight of the active base, including the cases where a salt is employed. Typically a dosage from about 0.5 mg/kg to about 5 mg/kg will be employed for intravenous or intramuscular administration. A dosage from about 10 mg/kg to about 50 mg/kg may be employed for oral administration.

The present invention is explained in greater detail in the following non-limiting Examples.

EXAMPLE 1

Fluorinated 2-Phenyl-4-Quinolones As Antimitotic Antitumor Agents

Fluorinated 2-phenyl-4-quinolone derivatives were synthesized and evaluated in NCI's 60 human tumor cell line in vitro screen. The results suggested that the ketone moiety played an essential role in activity. Among the compounds tested, 2'-fluoro-6-pyrrol-2-phenyl-4-quinolone (13) was found to exhibit the most potent cytotoxic activities (log $GI_{50}$<−8.00) against renal and melanoma tumor cell lines. Compound 13 was also a potent inhibitor of tubulin polymerization ($IC_{50}$=0.46 $\mu$M) and radiolabeled colchicine binding to tubulin, with activity comparable to those of the potent antimitotic natural products colchicine, podophyllotoxin, and combretastatin A-4.

A. Experimental

Melting points were determined on a Fisher-Johns melting point apparatus without correction. Elemental analyses were performed by Atlantic Microlabs, Atlanta, Ga. Optical rotations were determined with a DIP-1000 polarimeter. $^1$H-NMR spectra were measured on a Bruker AC-300 spectrometer with TMS as internal reference and $CDCl_3$ as solvent. Flash chromatography was performed on silica gel (mesh 25–150 $\mu$m) using a mixture of hexane-ethyl acetate as eluant.

2'-Fluoro-6,7-(methylenedioxy)-2-phenyl-4-quinolone (1). 2-Acetyl-4,5-(methylenedioxy)-aniline (3.0 mmol) was dissolved in 20 mL of THF and 10 mL of triethylamine. The mixture was cooled in an ice bath. A solution of 2-fluorobenzoyl chloride (3.0 mmol) was added dropwise. After 30 min at 0° C., the mixture was stirred at room temperature overnight and poured onto 50 mL of ice water. The precipitate was collected and washed successively with water and MeOH. The solid was dried under vacuum and then suspended in 20 mL of tert-butyl alcohol. Potassium tert-butoxide (1.17 g, 10.5 mmol) was added, and the mixture was heated under $N_2$ at 70° C. for 24 hrs. The mixture was cooled and poured onto 30 mL of aqueous $NH_4Cl$ solution. The solid was collected and washed successively with water and a mixture of $CHCl_3$ and MeOH (10:1). The crude product was recrystallized from a mixture of $CHCl_3$ and MeOH (20:1). $^1$H NMR (DMSO-$d_6$) $\delta$ 6.20 (s, 1H, H-3), 6.17 (s, 2H, $OCH_2O$), 7.09 (s, 1H, H-8), 7.43 (s, 1H, H-5), 7.44 (m, 2H, H-3', H-6'), 7.62, 7.69 (both t, J=7.5 Hz, 1H each, H-4', H-5'); Anal. ($C_{61}H_{10}FNO_3$) C, H, N.

2'-Fluoro-6,7-(methylenedioxy)-2-phenyl-4-(O-ethylacetate)quinoline (2). Compound 1 (283 mg, 1 mmol) was dissolved in dry DMF (12 mL), and NaH (60% in oil, 110 mg, 2.8 mmol) was added portionwise with stirring at 40° C. Ethyl chloroacetate (500 mg, 4.08 mmol) was added, and the reaction was stirred for 2 hrs at 60° C. The reaction mixture was poured onto ice water and filtered. The precipitate obtained was washed with water and recrystallized from $CH_2Cl_2$-MeOH to afford 260 mg of compound 2, yield 71.2%; mp 119–120° C.; $^1$H NMR ($CDCl_3$) $\delta$ 1.31 (t, J=3.7 Hz, 3H, $CH_3$), 4.32 (q, J=7.2 Hz, 2H, $CH_2CH_3$), 4.88 (s, 2H, $OCH_2COO$), 6.13 (s, 2H, $OCH_2O$), 7.04 (s, 1H, H-3), 7.17 (m, 1H, H-3'), 7.30 (m, 1H, H-5'), 7.40 (m, 1H, H-4'), 7.42 (s, 1H, H-8), 7.60 (s, 1H, H-5), 8.06 (m, 1H, H-6'); Anal. ($C_{20}H_{16}FNO_5$) C, H, N.

2'-Fluoro-6,7-(methylenedioxy)-2-phenyl-4-(O-acetic acid)quinoline (3). Compound 2 (160 mg, 0.44 mmol) was treated with aqueous NaOH (10%, 15 mL). The reaction mixture was refluxed for 2 hrs and cooled to room temperature. Aqueous HCl (10%) was added until pH 1~2. The resulting precipitate was harvested by filtration and recrystallized from MeOH/CHCl$_3$ to give a light yellow solid, compound 3, 130 mg, yield 87.0%; mp>300° C.; $^1$H NMR (DMSO-d$_6$) δ 5.18 (s, 2H, OCH$_2$COO), 6.33 (s, 2H, OCH$_2$O), 7.42 (s, 1H, H-3), 7.45 (s, 1H, H-8), 7.48 (m, 2H, H-3' and H-5'), 7.54 (s, 1H, H-5), 7.65 (m, 1H, H-4'), 7.91 (m, 1H, H-6'); Anal. (C$_{18}$H$_{12}$FNO$_5$.0.25H$_2$O) C, H, N.

2'-Fluoro-6,7-(methylenedioxy)-2-phenyl-4-(O-ethyl 4'-butyrate)quinoline (4). Obtained from compound 1 and ethyl 4-chlorobutyrate; yield 77.6%; mp 93–94° C; $^1$H NMR (CDCl$_3$) δ 1.27 (t, 3H, CH$_3$, J=7.0 Hz), 2.29 (m, 2H, CH$_2$CH$_2$CH$_3$), 2.62 (t,J=7.29 Hz, 2H, H-3'), 4.18 (q,J=7.0 Hz, 2H, OCH$_2$CH$_3$), 4.28 (q,J=6.0 Hz, 2H, OCH$_2$CH$_2$,), 6.12 (s, 2H, OCH$_2$O), 7.13 (s, 1H, H-3), 7.15–7.30 (m, 3H, H-3', H-4', H-5'), 7.41 (s, 1H, H-8), 7.46 (s, 1H, H-5), 8.02 (m, 1H, H-6'), Anal. (C$_{22}$H$_{20}$FNO$_5$) C, H, N.

2'-Fluoro-6,7-(methylenedioxy)-2-phenyl-4-(O-ethyl 4'-butylacetic acid)quinoline (5). Obtained by hydrolysis of 4 with aqueous NaOH using the same synthetic procedure as for 3; yield 82.5%; mp>300° C.; $^1$H NMR (DMSO-d$_6$) δ 2.10 (m, 2H, CH$_2$CH$_2$CH$_2$), 2.49 (t, 2H, CH$_2$COO), 4.29 (t, 2H, OCH$_2$), 6.22 (s, 2H, OCH$_2$O), 7.23 (s, 1H, H-3), 7.33 (m, 1H, H-3'), 7.35 (m, 1H, H-5'), 7.38 (s, 1H, H-8), 7.44 (s, 1H, H-5), 7.52 (m, 1H, H-4'), 7.95 (m, 1H, H-6'); Anal. (C$_{20}$H$_{16}$FNO$_5$) C, H, N.

2'-Fluoro-6,7-(methylenedioxy)-2-phenylquino-4-thione (6). Compound 1 (500 mg, 1.77 mmol) in 30 mL of dry toluene was stirred for a few minutes at room temperature, and Lawessen reagent (1.07 g, 2.65 mmol) was added with continued stirring. The mixture was stirred at 110–120° C. for 24 hrs and became clear with a deep orange color. The mixture was cooled to room temperature, poured into water, and extracted with CH$_2$Cl$_2$. The organic layer was dried over sodium sulfate and concentrated. Chromatography using CH$_2$Cl$_2$/CH$_3$OH as eluant afforded 430.6 mg of 6; yield 81.5%; mp 226–228° C.; $^1$H NMR (DMSO-d$_6$) δ 6.24 (s, 2H, OCH$_2$O), 7.18 (s, 1H, H-3), 7.33 (s, 1H, H-8), 7.50 (m, 2H, H-3', H-5'), 7.72 (m, 1H, H-4'), 7.77 (m, 1H, H-6'), 8.08 (s, 1H, H-5), 12.93 (s, 1H, NH); Anal. (C$_{16}$H$_{10}$FNO$_2$S.1.05 H$_2$O)C, H, N.

N-Boc-2'-fluoro-6,7-(methylenedioxy)-2-phenyl-4-quinolone (7). To a solution of 1 (283 mg, 1 mmol) in 6 mL of methylene chloride were added triethylamine (0.15 mL, 1 mmol), ditert-butyl dicarbonate (436 mg, 2 mmol), and 4-dimethylaminopyridine (61.25 mg, 1 mmol). The solution was stirred for 24 hrs at room temperature under N$_2$. The mixture was poured into water, extracted with CH$_2$Cl$_2$, and washed with water. The organic layer was dried over sodium sulfate and concentrated. Chromatography using EtOAc/hexane as eluant afforded 7; yield 86.8%; mp 118–120° C.; $^1$H NMR (CDCl$_3$) δ 1.61 (s, 9H, 3×CH$_3$), 6.14 (s, 2H, OCH$_2$O), 7.14 (m, 1H, H-3'), 7.20 (s, 1H, H-3), 7.29 (s, 1H, H-5), 7.40 (m, 1H, H-5'), 7.46 (s, 1H, H-8), 7.71 (m, 1H, H-4'), 8.07 (m, 1H, H-6'); Anal. (C$_{21}$H$_{18}$FNO$_5$) C, H, N.

2'-Fluoro-6-pyrroyl-2-phenyl-4-quinolone (13). 2-Amino-5-pyrroyl-acetophenone (8, 1 g, 4.9 mmol) was dissolved in 10 mL of THF and 2 mL of triethylamine. The mixture was cooled in an ice bath. A solution of 2-fluorobenzoyl chloride (855 mg, 5.39 mmol) was added dropwise. After 30 min at 0° C., the mixture was stirred at room temperature overnight and poured onto 50 mL of ice water. The precipitate was collected and washed successively with water and MeOH. The solid was dried under vacuum and suspended in 20 mL of tert-butyl alcohol. Potassium tert-butoxide (1.65 g, 14.7 mmol) was added, and the mixture was heated under N$_2$ at 70° C. for 16 hrs. The mixture was cooled and poured onto 30 mL of ice water. Aqueous 10% HCl was added to pH=6. The solid was collected and washed several times with water. The crude product was recrystallized from a mixture of CH$_2$Cl$_2$ and MeOH to afford 13; yield 59.3%; $^1$H NMR (DMSO-d$_6$) δ 2.01 (m, 4H, CH$_2$CH$_2$CH$_2$CH$_2$), 3.33 (m, 4H, CH$_2$CH$_2$CH$_2$CH$_2$), 6.04 (s, 1H, H-3), 7.04 (J=2.5 Hz, 1H, H-8), 7.10 (dd, J=2.5, 9.1 Hz, 1H, H-7), 7.39 (d, J=9.0 Hz, 1H, H-5), 7.43–7.71 (m, 4H, H-3', H-4', H-5', H-6'); Anal. (C$_{19}$H$_{17}$FN$_2$O·0.25 H$_2$O) C, H. N.

Compounds 1–7 and 13 were tested in National Cancer Institute's HTCL screen (M. Grever et al., *Seminars Oncol.* 1992, 19, 622–638; A. Monks et al., *J. Natl. Cancer Inst.* 1991, 83, 757–766). This assay involves determination of a test agent's effect on growth parameters against a panel of approximately 60 human tumor cell lines, mostly derived from solid tumors. The cytotoxic effects of each compound were expressed as log GI$_{50}$ values, which represents the log molar drug concentration required to cause 50% inhibition for selected tumor cell lines. These compounds were also assayed as inhibitors of tubulin polymerization, and the most active as inhibitors of [$^3$H]colchicine binding to tubulin.

The tubulin polymerization and [$^3$H]colchicine binding assays were performed as described previously (S. Kuo et al., *J. Med. Chem.* 1993, 36, 1146–1156). In the polymerization assay reaction mixtures contained 10 μM tubulin, and in the colchicine binding assay, 1.0 μM tubulin and 5.0 μM [$^3$H]colchicine.

B. Results and Discussion

The cytotoxic activities of 1–7 and 13 are summarized in Table 1 and effects on tubulin-based assays in Table 2. The results showed that the cytotoxicity decreased about 100-fold when the ketone form of 1 was converted to an enol ether (2–5). Compounds 2–5 lack both the amine H and the ketone O, the two functional moieties in the B ring, and these compounds had little or no effect on tubulin polymerization. Reduced cytotoxic activity was also found with 6, where only a thioketone moiety replaced the ketone group. Thioketone 6, like the enol ethers, had minimal effect on tubulin polymerization. These observations suggest that the ketone moiety plays a crucial role in the interaction of 2-phenyl-4-quinolone derivatives with tubulin and in the inhibition of cell growth that results from this interaction. Although the exact reason is uncertain, possible factors are steric and electronic influences and/or reduced H-bonding ability between drug and target protein. When a protecting group replaced the amine hydrogen, the resulting compound (7) showed interesting cytotoxic data. Compound 7 was equipotent with 1 against the HCT-116 colon, and OVCAR-3 ovarian cancer cell lines, was less active than 1 against the SF-295 CNS tumor cell line, and almost 20-fold more active than 1 against the NCI-H226 non-small cell lung cancer. These cells are among those that are exceptionally sensitive to antitubulin agents (K. Paull et al., *Cancer Res.* 1992, 52, 3892–3900), and 7 retained moderate activity as an inhibitor of tubulin polymerization. It is also possible that 7 undergoes intracellular conversion to a more active compound. The reduced interaction of 7 relative to 1 with tubulin could derive either from steric factors (bulky tert-butyl group) or loss of the amine hydrogen (altering H-bonding interactions with tubulin). The loss of antitubulin activities of N-methyl quinolone (15 vs 14, FIG. 1)(S. Kuo et al., *J. Med. Chem.* 1993, 36, 1146–1156) and of 2-phenylquinazolinone (17 vs 16)(E. Hamel et al., *Biochem. Pharmacol.* 1996, 51, 53–59) support the idea of a requirement for the N hydrogen. However, substantial enhancement of activity occurred when the phenyl group of inactive compound 17 was replaced by a styryl group (compound 18)(E. Hamel et al., *Biochem. Pharmacol.* 1996, 51, 53–59). This favors the loss of activity in 7 vs 1 being derived from factors, but it is also possibile that the binding site for 2-phenyl-4-quinolones and quinazolinones (phenyl C ring directly attached to the B ring) does not completely overlap here that the ketone functional moiety is essential for a strong interaction with tubulin, providing additional insight into the mechanism of ligand binding at the colchicine site. The ketone oxygen and, most importantly, the ketone form of the B ring appear to be involved in binding of this class of compound to tubulin. The amine hydrogen of the B ring also may be important for maximal antitubulin activity, suggested by the reduced activity of 7, but steric factors remain to be excluded as the explanation for the reduced activity of this compound.

TABLE 1

Inhibition of in vitro Tumor Cell Growth[a,b] by Fluorinated Quinolone Derivatives Cytotoxicity log $GI_{50}$ (M)[c]

| Compd | K562 | NCI-H226 | HCT116 | OVCAR-3 | RXF-393 | SK-Me15 | SF-268 | SF-295 | Mean log $GI_{50}$ |
|---|---|---|---|---|---|---|---|---|---|
| 1 | nt[d] | −6.35 | −7.22 | −7.09 | nt | −7.68 | −5.64 | −7.26 | −6.87 |
| 2 | −4.42 | >−4.00 | −4.14 | nt | >−4.00 | −4.14 | >−4.00 | >−4.00 | −4.10 |
| 3 | >−4.00 | >−4.00 | >−4.00 | >−4.00 | >−4.00 | >−4.00 | >−4.00 | >−4.00 | >−4.00 |
| 4 | −4.41 | −4.31 | >−4.00 | −4.82 | −4.60 | −4.24 | >−4.00 | −4.21 | −4.32 |
| 5 | −5.68 | −5.07 | −5.40 | −5.63 | −5.11 | −5.40 | −4.79 | −5.56 | −5.33 |
| 6 | −4.25 | −4.78 | −5.26 | −4.67 | −4.53 | −5.39 | −4.70 | −4.93 | −4.81 |
| 7 | >−4.00 | −7.60 | −7.35 | −7.49 | >−4.00 | nt | nt | −6.93 | −6.23 |
| 13 | −7.49 | −7.51 | −7.47 | −7.35 | <−8.00 | <−8.00 | −7.41 | −7.73 | −7.62 |

[a]Data obtained from NCI's in vitro disease-oriented human tumor cell screen.
[b]K-562, leukemia cell line;
NCI-H226, non-small cell lung cancer cell line;
HCT-116, colon cancer cell line;
OVCAR-3, ovarian cancer cell line;
RXF-393, renal cancer cell line;
RXF-393, renal cancer cell line;
SK-Me15, melanoma;
SF-286 and SF-295, CNS tumor cell lines.
[c]Log concentrations that reduced cell growth by 50%.
[d]"nt" means not tested the binding site of 2-styrylquinazolin-4(3H)-one (18) with a linker between the phenyl C ring and the B ring.

Among the new compounds, 13, a fluorinated quinolone with a heterocyclic ring at the 6-position, was the most potent in all assays. It was more cytotoxic than 1 in virtually all cases, especially against the RXF-393 renal and the SK-Mel5 melanoma cancer cells with log $GI_{50}$ values of <−8.00. Over all 60 cell lines, 13 was about 6-fold more active than 1, as shown by the mean log $GI_{50}$ values. In keeping with its greater cytotoxicity, 13 was more potent than 6 as an inhibitor of tubulin assembly, but the greater affinity of 13 relative to 6 was best demonstrated by its substantially greater activity as an inhibitor of the binding of [$^3$H]colchicine to tubulin. In the latter assay, 13 was nearly as active as the highly potent combretastatin A-4 (C. Lin et al., *Biochemistry* 1989, 28, 6984–6991).

Previously, 2-phenyl-4-quinolones were found to inhibit tubulin polymerization and the binding of radiolabeled colchicine to tubulin (C. Lin et al., *Biochemistry* 1989, 28, 6984–6991; S. Kuo et al., *J. Med. Chem.* 1993, 36, 1146–1156; S. Kuo et al., *J. Med. Chem.* 1993, 36, 1146–1156). Numerous compounds with various substitutions on the both A and C rings were studied. The "biaryl system", composed of rings A and C, is probably (Y. Xia et al., *J. Med. Chem.*, 1998, 41, 1155–1162) analogous to the similar biaryl system occurring in many antimitotic natural products, such as colchicine, podophyllotoxin or combretastatin A-4 (S. Hastie, *Pharm. & Ther.* 1991, 51, 377–401) (FIG. 1). However, the pharmacophores in the B ring of phenylquinolones, have been little explored, and we show

TABLE 2

Antitubulin Effects of Fluorinated Quinolone Derivatives

| | ITP[a] | ICB[b] (% inhib ± SD) | |
|---|---|---|---|
| Compound | $IC_{50}$ (μM) ± SD | 5 μM[c] | 1 μM[c] |
| 1 | 0.68 ± 0.02 | 39 ± 2 | |
| 2 | >40 | | |
| 3 | >20 | | |
| 4 | >40 | | |
| 5 | 12 ± 3 | | |
| 6 | 24 ± 2 | | |
| 7 | 3.2 ± 1 | | |
| 13 | 0.46 ± 0.003 | 93 ± 1 | 76 ± 5 |
| 14[d] | 7.3 ± 1 | | |
| 15[d] | >40 | | |
| 16[e] | 14 ± 0.9 | | |
| 17[e] | >40 | | |
| 18[e] | 5.0 ± 0.6 | | |
| Colchicine[f] | 0.80 ± 0.07 | | |
| Podophyllotoxin[f] | 0.46 ± 0.02 | | |
| Combretastatin A-4[f] | 0.53 ± 0.05 | 92 ± 3 | 88 ± 0.4 |

[a]ITP = inhibition of tubulin polymerization.
[b]ICB = inhibition of colchicine binding; evaluated only when polymerization $IC_{50}$ ≤ 1.0 μM.
[c]In the colchicine binding experiments, these values refer to the inhibitor concentration used. The [$^3$H] colchicine concentration was 5 μM, and the tubulin concentration was 1 μM.
[d]Data from S. Kuo et al., J. med. Chem. 1993, 36, 1146–1156. 6.
[e]Data from E. Hamel et al., biochem. Pharmacol. 1996, 51, 53–59.
[f]Data from Y. Xia et al., J. Med. Chem. 1998, 4, 1155–1162.

The foregoing is illustrative of the present invention, and is not to be construed as limiting thereof. The Invention is That which is claimed is:

1. A compound according to Formula I:

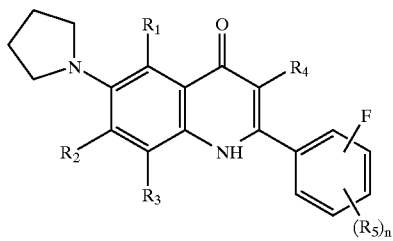

wherein:

F is substituted on the phenyl group at the ortho position;

$R_1$ is selected from the group consisting of H, lower alkyl, lower alkoxy, hydroxy, halo, and amino;

$R_2$ is is selected from the group consisting of H, lower alkyl, lower alkoxy, hydroxy, halo, and amino;

$R_3$ is selected from the group consisting of H, lower alkyl, lower alkoxy, hydroxy, halo, and amino;

$R_4$ is is selected from the group consisting of H, lower alkyl, lower alkoxy, hydroxy, halo, and amino;

$R_5$ is is selected from the group consisting of H, lower alkyl, lower alkoxy, hydroxy, halo, and amino; and n is from 0 to 4;

or a pharmaceutically acceptable salt thereof.

2. A compound according to claim 1, wherein $R_1$ is selected from the group consisting of H and lower alkyl.

3. A compound according to claim 1, wherein $R_2$ is selected from the group consisting of H and lower alkyl.

4. A compound according to claim 1, wherein $R_3$ is selected from the group consisting of H and lower alkyl.

5. A compound according to claim 1, wherein $R_4$ is selected from the group consisting of H and lower alkyl.

6. A compound according to claim 1, wherein $R_5$ is selected from the group consisting of H and lower alkyl.

7. A compound according to claim 1, wherein:

$R_1$ is selected from the group consisting of H and lower alkyl;

$R_2$ is selected from the group consisting of H and lower alkyl;

$R_3$ is selected from the group consisting of H and lower alkyl;

$R_4$ is selected from the group consisting of H and lower alkyl; and $R_5$ is selected from the group consisting of H and lower alkyl;

or a pharmaceutically acceptable salt thereof.

8. A compound according to claim 1, wherein n is 0 or 1.

9. A compound according to claim 1, wherein at least one of $R_1$, $R_2$, $R_3$, $R_4$, and $R_5$ is not H.

10. A compound according to claim 1 having the formula:

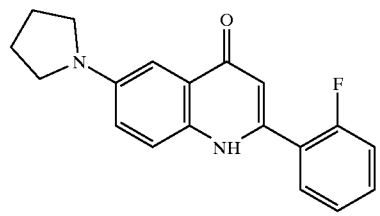

or a pharmaceutically acceptable salt thereof.

11. A pharmaceutical formulation comprising a compound according to claim 1, or a pharmaceutically acceptable salt thereof, in a pharmaceutically acceptable carrier.

12. A pharmaceutical formulation according to claim 11, wherein said carrier is an aqueous carrier.

13. A method for treating a tumor, comprising:

administering to a subject in need of such treatment a treatment effective amount of a compound of Formula I:

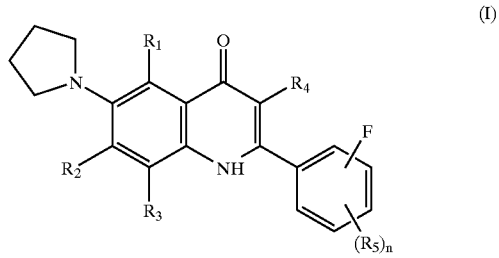

wherein:

$R_1$ is selected from the group consisting of H, lower alkyl, lower alkoxy, hydroxy, halo, and amino;

$R_2$ is is selected from the group consisting of H, lower alkyl, lower alkoxy, hydroxy, halo, and amino;

$R_3$ is is selected from the group consisting of H, lower alkyl, lower alkoxy, hydroxy, halo, and amino;

$R_4$ is is selected from the group consisting of H, lower alkyl, lower alkoxy, hydroxy, halo, and amino;

$R_5$ is is selected from the group consisting of H, lower alkyl, lower alkoxy, hydroxy, halo, and amino; and n is from 0 to 4;

or a pharmaceutically acceptable salt thereof.

14. A method according to claim 13, wherein said tumor is a solid tumor.

15. The method according to claim 13, wherein said tumor is selected from the group consisting of lung cancer, colon cancer, central nervous system cancers, melanoma, ovarian cancer, prostate cancer and breast cancer.

16. The method according to claim 13, wherein said tumor is breast cancer.

17. The method according to claim 13, wherein said tumor is prostate cancer.

18. A method of inhibiting cellular mitosis, comprising:

contacting a cell with a compound of Formula I:

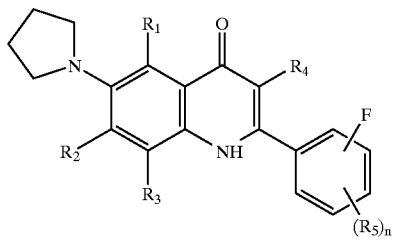

wherein:
R$_1$ is selected from the group consisting of H, lower alkyl, lower alkoxy, hydroxy, halo, and amino;
R$_2$ is is selected from the group consisting of H, lower alkyl, lower alkoxy, hydroxy, halo, and amino;
R$_3$ is is selected from the group consisting of H, lower alkyl, lower alkoxy, hydroxy, halo, and amino;
R$_4$ is is selected from the group consisting of H, lower alkyl, lower alkoxy, hydroxy, halo, and amino;
R$_5$ is is selected from the group consisting of H, lower alkyl, lower alkoxy, hydroxy, halo, and amino; and
n is from 0 to 4;

or a pharmaceutically acceptable salt thereof.

19. A method according to claim 18, wherein said contacting step is carried out in vivo.

20. A method according to claim 18, wherein said contacting step is carried out in vitro.

21. A compound having the formula:

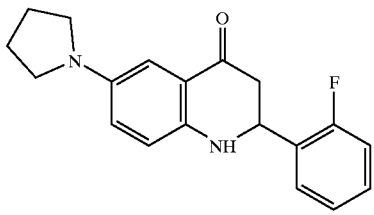

or a pharmaceutically acceptable salt thereof.

22. A pharmaceutical formulation comprising a compound according to claim 21, or a pharmaceutically acceptable salt thereof, in a pharmaceutically acceptable carrier.

23. A pharmaceutical formulation according to claim 22, wherein said carrier is an aqueous carrier.

24. A method for treating a tumor, comprising:
administering to a subject in need of such treatment a treatment effective amount of a compound according to Formula II,

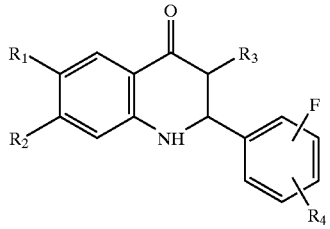

wherein:
R$_1$ is selected from the group consisting of H, hydroxy, lower alkyl, lower alkoxy, halo, amino, and heterocyclic rings;
R$_2$ is selected from the group consisting of H, hydroxy, lower alkyl, lower alkoxy, halo, and amino;
R$_3$ is selected from the group consisting of H, lower alkyl, lower alkoxy, halo, and amino; and
R$_4$ is selected from the group consisting of H, lower alkyl, lower alkoxy, halo, and amino;

or a pharmaceutically acceptable salt thereof.

25. A method according to claim 24, wherein said tumor is a solid tumor.

26. A method according to claim 24, wherein said tumor is selected from the group consisting of lung cancer, colon cancer, central nervous sytem cancers, melanoma, ovarian cancer, prostate cancer and breast cancer.

27. A method according to claim 24, wherein said tumor is breast cancer.

28. A method according to claim 24, wherein said tumor is prostate cancer.

29. A method of inhibiting cellular mitosis, comprising:
contacting a cell with a compound according to Formula II:

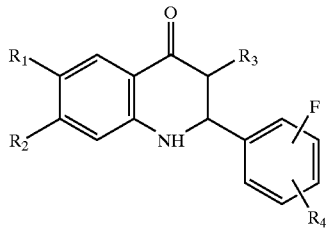

wherein:
R$_1$ is selected from the group consisting of H, hydroxy, lower alkyl, lower alkoxy, halo, amino, and heterocyclic rings;
R$_2$ is selected from the group consisting of H, hydroxy, lower alkyl, lower alkoxy, halo, and amino;
R$_3$ is selected from the group consisting of H, lower alkyl, lower alkoxy, halo, and amino; and
R$_4$ is selected from the group consisting of H, lower alkyl, lower alkoxy, halo, and amino;

or a pharmaceutically acceptable salt thereof.

30. A method according to claim 29, wherein said contacting step is carried out in vivo.

31. A method according to claim 29, wherein said contacting step is carried out in vitro.

* * * * *

UNITED STATES PATENT AND TRADEMARK OFFICE
CERTIFICATE OF CORRECTION

PATENT NO.   : 6,569,870 B1
DATED        : May 27, 2003
INVENTOR(S)  : Lee et al.

It is certified that error appears in the above-identified patent and that said Letters Patent is hereby corrected as shown below:

<u>Column 15,</u>
Line 15, please insert the following:
-- F is substituted on the phenyl group at the ortho position; --

Signed and Sealed this

Second Day of March, 2004

JON W. DUDAS
*Acting Director of the United States Patent and Trademark Office*